(12) United States Patent
Ogata

(10) Patent No.: US 8,048,911 B2
(45) Date of Patent: Nov. 1, 2011

(54) MELANIN ELIMINATOR PREPARATION

(75) Inventor: Kazumi Ogata, Toyonaka (JP)

(73) Assignee: OGA Research, Inc., Osaka (JP)

( * ) Notice: Subject to any disclaimer, the term of this patent is extended or adjusted under 35 U.S.C. 154(b) by 118 days.

(21) Appl. No.: 12/327,475

(22) Filed: Dec. 3, 2008

(65) Prior Publication Data

US 2009/0093541 A1   Apr. 9, 2009

Related U.S. Application Data

(62) Division of application No. 10/527,179, filed as application No. PCT/JP03/11676 on Sep. 11, 2003, now abandoned.

(30) Foreign Application Priority Data

Sep. 13, 2002 (JP) ................. 2002-307643

(51) Int. Cl.
*A61K 31/38* (2006.01)
(52) U.S. Cl. ...................................... 514/432
(58) Field of Classification Search .................. 514/432
See application file for complete search history.

(56) References Cited

U.S. PATENT DOCUMENTS

| | | | |
|---|---|---|---|
| 3,238,224 | A | 3/1966 | O'Hara et al. |
| 5,830,994 | A | 11/1998 | D'Hinterland et al. |
| 6,288,106 | B1 | 9/2001 | Pearson et al. |
| 6,331,559 | B1 | 12/2001 | Bingham et al. |
| 7,700,080 | B2 * | 4/2010 | Ogata et al. ............ 424/62 |
| 2002/0035243 | A1 | 3/2002 | Imfeld et al. |
| 2002/0107234 | A1 | 8/2002 | Bingham et al. |
| 2004/0092586 | A1 | 5/2004 | Ogata et al. |

FOREIGN PATENT DOCUMENTS

| | | |
|---|---|---|
| JP | S56-120611 | 9/1981 |
| JP | 60-11494 | 1/1985 |
| JP | 63-008316 A | 1/1988 |
| JP | 63-8316 | 1/1998 |
| JP | 2000-169371 | 6/2000 |
| WO | WO 95/08564 | 3/1995 |
| WO | WO 00/20385 | 4/2000 |
| WO | WO 00/24734 | 5/2000 |
| WO | WO 00/32235 | 6/2000 |
| WO | WO 01/49250 | 7/2001 |
| WO | WO 02/076935 | 10/2002 |

OTHER PUBLICATIONS

Barton et al., 2000, CAS: 132:302443.
Bonomi et al. Synthesis and characterization of iron derivatives of dihydrolipoic acid and dihydrolipoamide. *Inorganica Chimica Acta*, vol. 195, (1992) pp. 109-115.
Bonomi et al. Synthesis and characterization of metal derivatives of dihydrolipoic acid and dihydrolipoamide. *Inorganica Chimica Acta*, vol. 192 (1992), pp. 237-242.
Johannsen et al. Studies on the Relationship between Chemical Structure and Pharmacokinetics of Tc-Thiolato Complexes. *Nuc-Compact*, vol. 11, (1980), pp. 42-45. (English Abstract Provided).
Kijima et al. Electrochemical Study on Dihydrolipoamide-Iron (II) Complex and Its Chemical Reactivity. *J. Org. Chem.* vol. 50 (1985), pp. 2522-2524.
Oizumi et al., "Lipoamidase is a multiple hydrolase," *Biochem J.* (1990) 271. 45-49.
Sigel et al., "Stability and structure of binary and ternary complexes of α-Lipoate and lipoate derivatives with $Mn^{2+}$, $Cu^{2+}$, and $Zn^{2+}$ in solution." *Archives of Biochemistry and Biophysics* vol. 187, No. 1 (1978). 208-214.
Benedetto et al., "Role of Thiol compounds in mammalian melanin pigmentation. II. Gluathione and related enzymatic activities." *The Journal of Investigative Dermatology* vol. 79, No. 6 (1982). 422-424.
Noda et al., "Antioxidant activities of novel α-lipoic acid derivatives: N-(6, 8-dimeracaptoocatanoy)-2-aminoethanesulfonate- and N-(6, 8-dimercaptooctanoyl)-L-asparatete-zinc complex." CAS: 142: 403918.

* cited by examiner

*Primary Examiner* — Rei-tsang Shiao
(74) *Attorney, Agent, or Firm* — Merchant & Gould P.C.

(57) ABSTRACT

A melanin eliminator preparation comprising a metal chelate compound represented by the following formula (I),

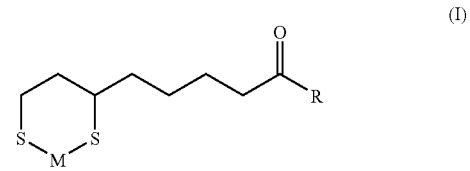

(I)

wherein M denotes a metal, and R denotes hydroxyl, O-lower alkyl, an amine bonded at N, an amino acid bonded at N, or a peptide bonded at N, or a pharmacologically acceptable salt thereof.

1 Claim, No Drawings

MELANIN ELIMINATOR PREPARATION

This application is a Divisional of U.S. application Ser. No. 10/527,179, filed Jan. 24, 2006, which is a National Stage Application of PCT/JP2003/11676, filed Sep. 11, 2003, which claims benefit of Serial No. JP 2002-307643, filed Sep. 13, 2002 in Japan and which application(s) are incorporated herein by reference. A claim of priority to all, to the extent appropriate is made.

TECHNICAL FIELD

The present invention relates to a novel and useful melanin eliminator preparation comprising a 6,8-dimercaptooctanoic acid metal chelate compound, derivatives thereof or pharmacologically acceptable salts thereof.

BACKGROUND ART 6,8-dimercaptooctanoic acid is the reduced form of α-lipoic acid, a coenzyme occurring in mitochondria, and has an ability of restoring reduced forms of glutathione or vitamin C back from their oxidized forms. However, 6,8-dimercaptooctanoic acid is so unstable in the air that it is oxidized back to α-lipoic acid.

A group of α-lipoylamino acids are described in Japanese Patent Publication No. S42-1286 (corresponding U.S. Pat. No. 3,238,224), in which glycine, methionine, glutamic acid, valine or the like, respectively, is bonded to α-lipoic acid.

An imidazole salt of α-lipoylaminoethylsulfonic acid is described in Example 24 in Japanese Patent Application Publication No. 2000-169371.

A pharmaceutical preparation for external use containing a lipoamide as an active ingredient is disclosed in Japanese Patent Application Publication No. S63-8316.

Other lipoic acid derivatives such as lipoyl esters are also known (Biochem. J. (1990) 271, 45-49).

Further, metal derivatives of dihydrolipoic acid and dihydrolipoamide are also known (Inorganica Chimica Acta, 192 (1992) 237-242)(J. Org. Chem. 1985, 50 2522-2524).

In the abovementioned situation, the present inventor found as a result of repeated studies that 6,8-dimercaptooctanoic acid metal chelate compounds, derivatives thereof and pharmacologically acceptable salts thereof have a melanin eliminating effect, i.e., that simple external application of the present compound to the skin under which aggregated melanin pigment is deposited, eliminates melanin without giving any damage to the skin, thus completed the present invention.

The present invention provides a melanin eliminator preparation comprising a 6,8-dimercaptooctanoic acid metal chelate compound, a derivative thereof or a pharmacologically acceptable salt thereof.

DISCLOSURE OF INVENTION

The present invention relates to:

a melanin eliminator preparation comprising a metal chelate (or a metal complex) compound represented by the following formula (I) (hereinafter also referred to as "the present compound"),

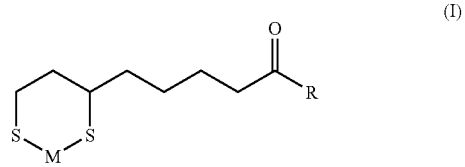

(I)

wherein M denotes a metal, and R denotes hydroxyl, O-lower alkyl, an amine bonded at N, an amino acid bonded at N, or a peptide bonded at N, or a pharmacologically acceptable salt thereof.

(2) The melanin eliminator preparation defined in (1) above wherein the metal chelate compound is 6,8-dimercaptooctanoic acid metal chelate compound.

(3) The melanin eliminator preparation defined in (1) above wherein the metal chelate compound is a 6,8-dimercaptooctanoic acid lower alkyl ester metal chelate compound.

(4) The melanin eliminator preparation defined in (3) above wherein the 6,8-dimercaptooctanoic acid lower alkyl ester metal chelate compound is a 6,8-dimercaptooctanoic acid ethyl ester metal chelate compound.

(5) The melanin eliminator preparation defined in (1) above wherein the metal chelate compound is a N-(6,8-dimercaptooctanoyl)amine metal chelate compound.

(6) The melanin eliminator preparation defined in (5) above wherein the N-(6,8-dimercaptooctanoyl)amine metal chelate compound is selected from the group consisting of 6,8-dimercaptooctanoic acid amide metal chelate, N-(6,8-dimercaptooctanoyl)-2-aminoethanol metal chelate, N-(6,8-dimercaptooctanoyl)isopropylamine metal chelate, N-(6,8-dimercapto-octanoyl)melatonin metal chelate, and N-(6,8-dimercaptooctanoyl)-2-amino-pyridine metal chelate.

(7) The melanin eliminator preparation defined in (1) above wherein the metal chelate compound is a N-(6,8-dimercaptooctanoyl)amino acid metal chelate compound.

(8) The melanin eliminator preparation defined in (7) above wherein the N-(6,8-dimercaptooctanoyl)amino acid metal chelate compound is selected from the group consisting of N-(6,8-dimercaptooctanoyl)-α-amino acid metal chelate, N-(6,8-dimercaptooctanoyl)-ω-amino acid metal chelate, and N-(6,8-dimercaptooctanoyl)-special amino acids metal chelate compound.

(9) The melanin eliminator preparation defined in (8) above wherein the N-(6,8-dimercaptooctanoyl)-α-amino acid metal chelate is selected from the group consisting of N-(6,8-dimercaptooctanoyl) glycine metal chelate, N-(6, 8-dimercaptooctanoyl)alanine metal chelate, N-(6,8-dimercapto-octanoyl)threonine metal chelate, N-(6,8-dimercaptooctanoyl)serine metal chelate, N-(6,8-dimercaptooctanoyl) aspartic acid metal chelate, N-(6,8-di-mercaptooctanoyl) glutamic acid metal chelate, N-(6,8-dimercapto-octanoyl) phenylalanine metal chelate, N-(6,8-dimercaptooctanoyl) methionine metal chelate, N-(6,8-dimercaptooctanoyl) norleucine metal chelate, N-(6,8-di-mercaptooctanoyl) cysteine metal chelate, N-(6,8-dimercaptooctanoyl)-hydroxyproline metal chelate, N-(6,8-dimercaptooctanoyl) histidine metal chelate, N-(6,8-dimercaptooctanoyl)-5-hydroxytryptophan metal chelate, N-(6,8-dimercaptooctanoyl) penicillamine metal chelate and N-(6,8-dimercaptooctanoyl)lysine metal chelate compounds.

(10) The melanin eliminator preparation defined in (9) above wherein the N-(6,8-dimercaptooctanoyl)-ω-amino acid metal chelate and the N-(6,8-dimercaptooctanoyl)special amino acid metal chelate compounds are selected from the group consisting of N-(6,8-dimercaptooctanoyl)-3- amino-propionic acid metal chelate, N-(6,8-dimercaptooc-tanoyl)-4-aminobutyric acid metal chelate, N-(6,8-dimercaptooctanoyl)-6-aminohexanoic acid metal chelate, N-(6,8-dimercaptooctanoyl)-4-trans-aminomethyl-1-cyclohexane carboxylic acid metal chelate, N-(6,8-dimercaptooctanoyl)-2-aminoethanesulfonic acid metal chelate, N-(6,8-dimercaptooctanoyl) sulfanilic acid metal chelate, N-(6,8-di-mercaptooctanoyl)anthranilic acid metal chelate and N-(6,8-dimercapto-octanoyl)anthranilic acid ethyl ester metal chelate compounds.

(11) The melanin eliminator preparation defined in (1) above wherein the metal chelate compound is a N-(6,8-dimercaptooctanoyl)peptide metal chelate compound.

(12) The melanin eliminator preparation defined in (11) above wherein the N-(6,8-dimercaptooctanoyl)peptide metal chelate compound is selected from the group consisting of N-(6,8-dimercaptooctanoyl)aspartylglycine metal chelate and N-(6,8-dimercaptooctanoyl)threonylglycine metal chelate.

(13) The melanin eliminator preparation defined in one of (1) to (12) above wherein the metal is zinc.

(14) The melanin eliminator preparation defined in one of (1) to (13) above wherein the preparation is a dermatological preparation for external use.

(15) The melanin eliminator preparation defined in (14) above wherein the preparation is a cosmetic preparation.

(16) A zinc chelate compound represented by the following formula (II),

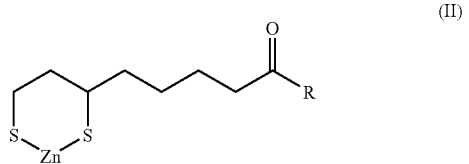

(II)

wherein R denotes hydroxyl, O-alkyl, an amine bonded at N or a peptide bonded at N, or a pharmacologically acceptable salt thereof.

(17) The zinc chelate compound defined in (16) above wherein the compound is a 6,8-dimercaptooctanoic acid zinc chelate compound, or a pharmacologically acceptable salt thereof.

(18) A method for elimination of melanin comprising administering to a human an effective amount of a metal chelate compound represented by the following formula (I),

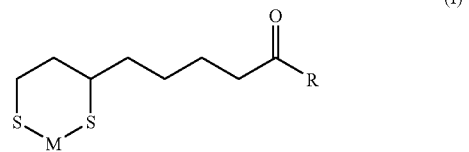

(I)

wherein M denotes a metal, and R denotes hydroxyl, O-lower alkyl, an amine bonded at N, an amino acid bonded at N or a peptide bonded at N, or a pharmacologically acceptable salt thereof.

(19) Use of a metal chelate compound represented by the following formula (I),

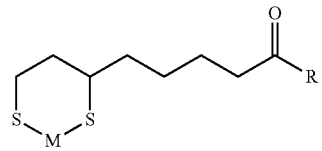

(I)

wherein M denotes a metal, and R denotes hydroxyl, O-lower alkyl, an amine bonded at N, an amino acid bonded at N or a peptide bonded at N, or a pharmacologically acceptable salt thereof for the manufacture of a melanin eliminating preparation.

BEST MODE FOR CARRYING OUT THE INVENTION

Examples of the metal of the metal chelate compound contained in the melanin eliminator preparation of the present invention include zinc, cobalt, iron and germanium, among which zinc is preferred.

In the present invention, examples of the lower alkyl include linear or branched alkyl having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, 2-methylpentyl, 3-methylpentyl, 4-methylpentyl, 2,2-dimethylbutyl, 3,3-dimethylbutyl, 2-ethylbutyl, etc. among which methyl and ethyl are preferred.

In the present invention, an "amine" means a compound obtained by replacing 1-2 hydrogen atoms of ammonia $NH_3$ with an aliphatic hydrocarbon group having 1-5 carbon atoms that may be substituted with a hydroxyl group, or a compound obtained by replacing 1-2 hydrogen atoms of ammonia with a nitrogen-containing hetero ring including pyridine ring, a pyrimidine ring or an indole ring that may be substituted. Specifically, 2-aminoethanol, isopropylamine, melatonin, 2-aminopyridine, etc. are included.

In the present invention, an "amino acid" means a co-amino acid having a carboxyl group and an amino acid in the same molecule, such as α-amino acid, β-amino acid, γ-amino acid, δ-amino acid, ε-amino acid, etc., such a special amino acid as aminomethylcyclohexanecarboxylic acid, anthranilic acid and anthranilic acid ethyl ester, as well as a special amino acid that has a sulfonic acid group and an amino acid in the same molecule such as aminoethanesulfonic acid (taurine) and p-aminobenzenesulfonic acid (sulfanilic acid). Examples of α-amino acid include glycine, alanine, valine, leucine, isoleucine, serine, threonine, tyrosine, cysteine, methionine, aspartic acid, asparagine, glutamic acid, glutamine, arginine, lysine, histidine, phenylalanine, tryptophan, etc. Examples of β-amino acid include β-alanine, examples of γ-amino acid include γ-amino-L-butyric acid (GABA) and carnitine. Examples of δ-amino acid include 5-aminolevulinic acid and 5-aminovaleric acid. Examples of ε-amino acid include 6-aminohexanoic acid. Among those amino acids, anthranilic acid, aminoethanesulfonic acid, methionine, histidine, lysine, phenylalanine, γ-amino-L-butyric acid and 6-aminohexanoic acid are preferred.

In the present invention, a "peptide" means a dipeptide which is formed from two amino acids (as defined above), which may be the same or different, by acid amide bond between a carboxyl group of one amino acid and an amino group of the other amino acid, e.g., aspartylglycine and threonylglycine, etc.

Examples of a pharmacologically acceptable salt of the present compound include alkali metal salts such as sodium salt and potassium salt, as well as alkali earth metal salt such as calcium salt and magnesium salt. However, any other salts may be employed as desired for the purpose of the present invention insofar as they are pharmacologically acceptable.

Referring for example to a zinc chelate compound, a method for preparation of 6,8-dimercaptooctanoic acid metal chelate compounds, and their derivatives, contained in the melanin eliminator preparation of the present invention will be described below.

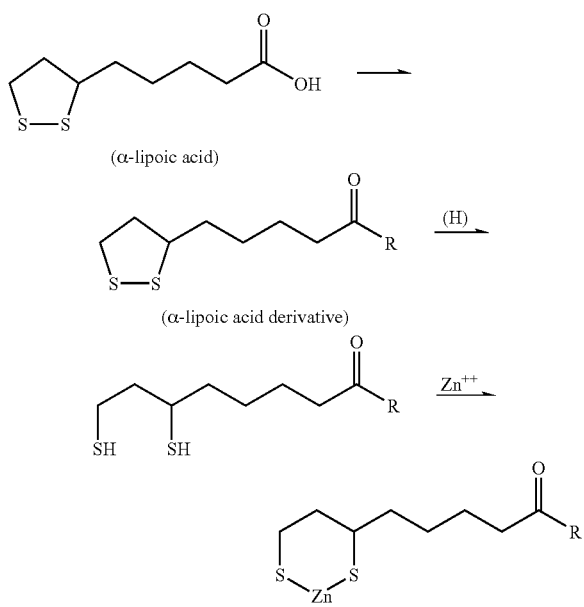

(wherein R denotes hydroxyl, an O-lower alkyl, an amine bonded at N or a peptide bonded at N)

By reducing an α-lipoic acid or an α-lipoic acid amide with zinc and hydrochloric acid (or acetic acid), 6,8-dimercaptooctanoic acid zinc chelate or its amide-form compound, respectively, is synthesized. In addition, 6,8-dimercaptooctanoic acid ethyl ester zinc chelate, for example, is obtained by reduction of α-lipoic acid ethyl ester in the same manner. Further, as for N-(6,8-dimercaptooctanoyl)amines, N-(6,8-dimercaptooctanoyl)amino acids or N-(6,8-dimercaptooctanoyl)peptides, α-lipoic acid, for example, is dissolved in chloroform or acetonitrile, and then coupled with an amine, amino acid or peptide by the mixed acid anhydride method using ethyl chloroformate in the presence of triethylamine to form N-α-lipoylamine, N-α-lipoylamino acid or N-α-lipoylpeptide. Reduction of them with zinc and acetic acid (or hydrochloric acid) gives the respective aimed compounds. Furthermore, where the amino acid or peptide derivatives are to be converted to alkali salts, for example, their free acids are dissolved, or suspended in water and then dissolved through neutralization with alkali hydroxide. Condensation followed by collection by filtration of crystals precipitated after addition of alcohol gives the salt of the aimed compounds in high yield.

Reduced form compounds of α-lipoic acids and α-lipoic acid derivatives, i.e., 6,8-dimercaptooctanoic acids and their derivatives, are very unstable in the air. However, chelation of them with a metal, e.g., zinc, results in the formation of a six-membered ring and gives crystalline, stable compounds. The present compound, furthermore, has a potent reducing activity as well as a potent radical scavenging activity, and, as originating from the living body, it is a highly safe compound.

According to the mechanism of formation of melanin, which makes the basis of blotches and freckles, free radicals are first produced in the skin by the action of ultraviolet light, stimulation by this then activates melanocytes, thus activating the function of tyrosinase in the melanocytes, and this leads to melanin formation through several chemical steps including oxidation and polymerization of tyrosine. The action of most skin whitening agents are prevention of melanin formation by their inhibitory effect on the enzyme tyrosinase.

However, as a result of the studies, the present inventor found that the present compound has an effect to eliminate already-formed and deposited aggregated melanin pigment (blotches, freckles, lentigines). Thus, this effect is considered to be based on a mechanism other than tyrosinase inhibitory action or elastase inhibitory action.

There are several methods for removing lentigines, such as surgical operation, potassium hydroxide/starch or liquid nitrogen method, etc., all of which give damages to the skin. In recent years, a method is known in which selective destruction of melanin-containing cells is caused with laser. However, as laser treatment itself causes inflammation during irradiation, this entails concerns of recurrence.

For the purpose of eliminating melanin, the compound of the present invention is applied in the form of ointments, cosmetic preparations or lotions.

According to the observations of the healing effect of the present compound, there are cases in which melanin pigment gradually fades in color from black to pale umber and the other cases in which melanin migrates to the corneal layer of epidermis and finally lost with the dirt on the skin. If this means that the melanin in the cells is recognized as a xenobiotic and pushed out as a result of enhanced immunity, it also suggests a possible application to cancer cells.

Though it depends on the degree of the blotches or lentigines, as evident from the examples described below, the effect of the present compound was observed, i.e., for example, a lotion containing 0.5 (w/w)% of N-(6,8-dimercaptooctanoyl)-3-aminopropionic acid sodium/zinc chelate or N-(6,8-dimercaptooctanoyl)anthranilic acid sodium/zinc chelate compound applied one or two times daily showed satisfactory effects in about one month, exhibiting either fading of the color from black to pale umber or falling off as a scab in the cases of blotches and lentigines located closest to the corneal layer of epidermis, though in the case of lentigines it depended on which area they were placed, e.g., on the face, arms, etc. The effect was also noted on blotches formed on the acne scars, showing clear difference compared with the pre-treatment conditions.

These findings revealed that the present compound has the activity of eliminating melanin pigment.

Concentrations of the present compound in use are usually 0.001-5 (w/w)%, and preferably 0.01-1.0 (w/w)% in the case of a cream, and usually 0.001-5 (w/v)%, and preferably 0.01-1.0 (w/v)% in the case of an aqueous solution or a lotion.

Ingredients usually employed in cosmetics or dermatological external preparations, e.g., diluents, pigments, perfume materials, ultraviolet light absorbents, antioxidants, stabilizers, preservatives, etc. may be added as desired to the melanin eliminator preparation of the present invention.

As desired and in accordance with the purpose and need, the melanin eliminator preparation of the present invention may contain one or more species of the present compound in combination.

EXAMPLES

The present invention will be described below referring to Reference Examples, examples and Test Examples. However, the present invention is not limited to those examples.

Reference Examples 1-9, Examples 1-12, and 19, 20

General method for preparation of N-(6,8-dimercaptooctanoyl)amino acid (or peptide) sodium/zinc chelate compounds 4.2 g (0.02 mol) of DL-α-lipoic acid and 2.4 g (0.023 mol) triethylamine are dissolved in 40 ml of acetonitrile and let stand with stirring at −5° C. To this is gradually added dropwise 2.4 g (0.022 mol) of ethyl chloroformate, and 20 minutes after completion of this dropwise addition, a solution of 1.0-2.0 g of sodium hydroxide and about 0.023 mol of an amino acid (or a peptide) in about 50 ml of methanol (or 70% methanol aqueous solution) is quickly added, and stirring is continued for 30 minutes and, for further one hour at room temperature. Evaporation of the solvent under reduced pressure gives a salt of N-(α-lipoyl)amino acid (or peptide).

To this are then added 50 ml of a 60% acetic acid aqueous solution and 2.5 g of zinc powder, and, after 1-5 hours of stirring under heating at 50° C., unreacted zinc is separated out by filtration, and the filtrate is concentrated. After addition of water (or methanol), precipitated crystals are collected by filtration, and washed with water. The crystals are suspended in water and then dissolved at pH 9-10 with addition of alkali hydroxide in order to form an alkali salt. Insoluble matters are removed by filtration and the filtrate is concentrated, and, after addition of alcohol, precipitated crystals are collected by filtration, they are then recrystallized from a proper solvent, such as water/alcohol.

Reference Example 1

N-(6,8-dimercaptooctanoyl)glycine sodium/zinc chelate compound

Using 4.2 g of DL-α-lipoic acid and 1.9 g of glycine, 3.9 g of white crystals of the aimed compound were obtained via N-α-lipoylglycine sodium salt (mp. 218-220° C.). mp: decomp. starting at about. 297° C. TLC, Rf=0.64 (chloroform/methanol/water=5/4/1)

Reference Example 2

N-(6,8-dimercaptooctanoyl)aspartic acid monosodium/zinc chelate compound

Using 4.2 g of DL-α-lipoic acid and 2.9 g of L-aspartic acid, 4.2 g of white crystals of the aimed compound were obtained via N-α-lipoylaspartic acid sodium salt (mp. over 300° C.). mp: decomp. starting at about 295° C. TLC, Rf=0.53 (chloroform/methanol/water=5/4/1).

Reference Example 3

N-(6,8-dimercaptooctanoyl)methionine zinc chelate compound

Using 4.2 g of DL-α-lipoic acid and 3.5 g of L-methionine, 2.8 g of white crystals of the aimed compound was obtained via N-α-lipoylmethionine (mp. 108-109° C.). mp: decomp. starting at about 260° C. TLC, Rf=0.82 (n-butanol/acetic acid/water=4/1/2)

Reference Example 4

N-(6,8-dimercaptooctanoyl)cysteine zinc chelate compound

Using 4.2 g of DL-α-lipoic acid and 2.6 g of L-cysteine, 4.1 g of white crystals of the aimed compound were obtained via N-α-lipoylcysteine sodium salt (mp: decomp. starting at about 150° C.). mp: decomp. starting at about 280° C. TLC, Rf=0.71 (chloroform/methanol/water=5/4/1).

Reference Example 5

N-(6,8-dimercaptooctanoyl)phenylalanine sodium/zinc chelate compound

Using 4.2 g of DL-α-lipoic acid and 3.5 g of L-phenylalanine, 3.9 g of white crystals of the aimed compound were obtained via N-α-phenylalanine (mp. 154-156° C.). mp: decomp. starting at about 270° C. TLC, Rf=0.82 (n-butanol/acetic acid/water=4/1/2).

Reference Example 6

N-(6,8-dimercaptooctanoyl)-4-aminobutyric acid sodium/zinc chelate compound

Using 4.2 g of DL-α-lipoic acid and 2.3 g of 4-aminobutyric acid, 5.2 g of white crystals of the aimed compound were obtained via N-α-lipoyl-4-aminobutyric acid (mp: decomp. starting at about 235° C.). mp: decomp. starting at about 297° C. TLC, Rf=0.70 (chloroform/methanol/water 5/4/1).

Reference Example 7

N-(6,8-dimercaptooctanoyl)-6-aminohexanoic acid sodium/zinc chelate compound

Using 4.2 g of DL-α-lipoic acid and 3.0 g of 6-aminohexanoic acid, 2.0 g of white crystals of the aimed compound were obtained via N-α-lipoyl-6-aminohexanoic acid sodium salt (mp. 200-202° C.). mp: decomp. starting at about 295° C. TLC, Rf=0.84 (chloroform/methanol/ water=5/4/1).

Reference Example 8

N-(6,8-dimercaptooctanoyl)anthranilic acid sodium/zinc chelate compound

Using 4.2 g of DL-α-lipoic acid and 2.9 g of anthranilic acid, 2.1 g of white crystals of the aimed compound were obtained via N-α-lipoylanthranilic acid sodium salt (mp. over 300° C.). mp: decomp. starting at about 290° C. TLC, Rf=0.88 (n-butanol/acetic acid/water=4/1/2).

Reference Example 9

N-(6,8-dimercaptooctanoyl)-2-aminoethanesulfonic acid sodium/zinc chelate compound Using 6.2 g of DL-α-lipoic acid and 4.5 g of 2-aminoethanesulfonic acid, 4.5 g of white crystals of the aimed compound were obtained via N-α-lipoylaminoethanesulfonic acid sodium salt (mp. 235-237° C.). mp: decomp. starting at about 293° C. TLC, Rf=0.51 (n-butanol/acetic acid/water=4/1/2).

Example 1

N-(6,8-dimercaptooctanoyl)hydroxyproline sodium/zinc chelate compound

From 4.2 g of DL-α-lipoic acid and 2.8 g of L-4-hydroxyproline, 4.9 g of white crystals of the aimed compound were obtained. mp. over 300° C. TLC, Rf=0.66 (n-butanol/acetic acid/water=4/1/2).

Example 2

N-(6,8-dimercaptooctanoyl)histidine sodium/zinc chelate compound

From 4.2 g of DL-α-lipoic acid and 3.4 g of L-histidine, 5.8 g of white crystals of the aimed compound were obtained. mp. over 300° C. TLC, Rf=0.39 (n-butyanol/acetic acid/water=4/1/2). mp. over 300° C., TLC, Rf=0.39 (n-butanol/acetic acid/water=4/1/2).

Example 3

N-(6,8-dimercaptooctanoyl)glutamic acid sodium/zinc chelate compound

From 4.2 g of DL-α-lipoic acid and 3.5 g of L-glutamic acid, 5.7 g of white crystals of the aimed compound were obtained. mp. over 300° C. TLC, Rf=0.74 (n-butanol/acetic acid/water=4/1/2).

Example 4

N-(6,8-dimercaptooctanoyl)threonine sodium/zinc chelate compound

From 4.2 g of DL-α-lipoic acid and 2.6 g of L-threonine, 5.5 g of white crystals of the aimed compound were obtained. mp. over 300° C. TLC, Rf=0.73 (n-butanol/acetic acid/water=4/1/2).

Example 5

N-(6,8-dimercaptooctanoyl)alanine sodium/zinc chelate compound

From 4.2 g of DL-α-lipoic acid and 2.1 g of L-alanine, 5.4 g of white crystals of the aimed compound were obtained. mp: decomp. starting at about 290° C. TLC, Rf=0.78 (n-butanol/acetic acid/water=4/1/2).

Example 6

N-(6,8-dimercaptooctanoyl)serine sodium/zinc chelate compound

From 4.2 g of DL-α-lipoic acid and 2.4 g of L-serine, 5.0 g of white crystals of the aimed compound were obtained. mp: gradual decomp. starting at about 285° C. TLC, Rf=(n-butanol/acetic acid/water=4/1/2).

Example 7

N-(6,8-dimercaptooctanoyl)norleucine sodium/zinc chelate compound

From 4.2 g of DL-α-lipoic acid and 3.0 g of L-norleucine, 5.1 g of white crystals of the aimed compound were obtained. mp. gradual decomp. starting at about 295° C. TLC, Rf=0.90 (n-butanol/acetic acid/water=4/1/2).

Example 8

N-(6,8-dimercaptooctanoyl)-5-hydroxytryptophan sodium/zinc chelate compound

From 4.2 g of DL-α-lipoic acid and 5.0 g of L-5-hydroxytryptophan, 6.5 g of grayish white crystals of the aimed compound were obtained. mp: decomp. starting at about 290° C. TLC, Rf=0.81 (n-butanol/acetic acid/water=4/1/2).

Example 9

N-(6,8-dimercaptooctanoyl)penicillamine sodium/zinc chelate compound

From 4.2 g of DL-α-lipoic acid and 3.5 g of penicillamine, 6.0 g of white crystals of the aimed compound were obtained. mp: gradual decomp. starting at about 280° C. TLC, Rf=0.80 (n-butanol/acetic acid/water=4/1/2).

Example 10

N-(6,8-dimercaptooctanoyl)-3-aminopropionic acid sodium/zinc chelate compound From 4.2 g of DL-α-lipoic acid and 2.0 g of 6-alanine, 5.8 g of white crystals of the aimed compound were obtained. mp: gradual decomp. starting at about 295° C. TLC, Rf=0.83 (n-butanol/acetic acid/water=4/1/2).

Example 11

N-(6,8-dimercaptooctanoyl)-4-transaminomethyl-1-cyclohexane-carboxylic acid sodium/zinc chelate compound From 4.2 g of DL-α-lipoic acid and 3.5 g of 4-trans-aminomethylcyclohexanecarboxylic acid, 5.8 g of white crystals of the aimed compound were obtained. mp: gradual decomp. starting at about 297° C. TLC, Rf=0.81 (n-butanol/acetic acid/water=4/1/2).

Example 12

N-(6,8-dimercaptooctanoyl)sulfanilic acid sodium/zinc chelate compound

From 4.2 g of DL-α-lipoic acid and 3.8 g of sulfanilic acid, 5.4 g of white crystals of the aimed compound were obtained. mp. over 300° C. TLC, Rf=0.57 (n-butanol/acetic acid/water=4/1/2).

Example 13

N-(6,8-dimercaptooctanoyl)isopropylamine zinc chelate compound 4.2 g of DL-α-lipoic acid and 2.4 g of triethylamine were dissolved in 50 ml of acetonitrile and cooled down to −65° C. with stirring. To this was gradually added 2.4 g of ethyl chloroformate dropwise. Twenty minutes after the completion of the dropwise addition, 1.5 g of isopropylamine dissolved in 30 ml of acetonitrile was quickly added, and stirring was continued for 30 minutes and, further one hour at room temperature. The solvent was evaporated under reduced pressure, and water was added to the residue and the mixture then was cooled down. Precipitated pale yellow crystals were collected by filtration, dissolved in 60 ml of tetrahydrofuran (THF). To this were added 20 ml of 50% acetic acid aqueous solution and 2.0 g of zinc powder and reaction was allowed for two hours at 50° C. with stirring. Unreacted zinc was separated out by filtration, and the filtrate was concentrated. After addition of water to the residue, precipitated white crystals were collected by filtration. Recrystallized from THF/acetic acid/water gave 5.0 g of the aimed compound. mp. 271-273° C. TLC, Rf=0.89 (n-butanol/acetic acid/water=4/1/2).

Example 14

N-(6,8-dimercaptooctanoyl)-2-aminoethanol zinc chelate compound

Using 4.2 g of DL-α-lipoic acid and 1.5 g of monoethanolamine, 4.2 g of white crystals of the aimed compound were obtained by the same method as in Example 13. mp: gradual decomp. starting at about 298° C. TLC, Rf=0.77 (n-butanol/acetic acid/water=4/1/2).

Example 15

N-(6,8-dimercaptooctanoyl)melatonin zinc chelate compound

Using 4.2 g of DL-α-lipoic acid and 4.0 g of melatonin, 6.5 g of white crystals of the aimed compound were obtained by the same method as in Example 13. mp. 210-212° C. TLC, Rf=0.84 (n-butanol/ acetic acid/water=4/1/2).

Example 16

N-(6,8-dimercaptooctanoyl)-2-aminopyridine zinc chelate compound

Using 4.2 g of DL-α-lipoic acid and 2.2 g of 2-aminopyridine, 5.3 g of white crystals of the aimed compound were obtained by the same manner as in Example 13. mp. 243-245° C. TLC, Rf=0.87 (n-butanol/acetic acid/water=4/1/2).

Example 17

N-(6,8-dimercaptooctanoyl)anthranilic acid ethyl ester zinc chelate compound

Using 4.2 g of DL-α-lipoic acid and 3.6 g of anthranilic acid ethyl ester, 4.6 g of white crystals of the aimed compound (recrystallized from THF/acetic acid/water) were obtained. mp. gradual decomp. starting at about 290° C. TLC, Rf=0.88 (n-butanol/acetic acid/water).

Example 18

$N^\epsilon$-(6,8-dimercaptooctanoyl)lysine zinc chelate compound

A mixed acid anhydride was prepared from 4.2 g of DL-α-lipoic acid, 2.4 g of triethylamine and 2.4 g of ethyl chloroformate in 50 ml of acetonitrile under cooling. To this were added a solution of 3.1 g of L-lysine, 5.5 g of copper sulfate (pentahydrate) and 2.0 g of sodium hydroxide in 60 ml of water, and reaction was allowed. Precipitated $N^\epsilon$-(α-lipoyl) lysine cupper salt was collected by filtration, and washed with water and methanol. This was suspended in 70% acetic acid aqueous solution and cupper was converted to copper sulfide with hydrogen sulfide and removed by filtration. The filtrate was concentrated, methanol was added to the residue, and precipitated pale yellow crystals were collected by filtration. mp. 254-255° C., Yield: 3.5 g.

This was then dissolved in 60% acetic acid aqueous solution and 2.0 g of zinc powder was added. After 3 hours of stirring at 50° C. and removal of the zinc by filtration, the filtrate was concentrated. Addition of methanol to this and collection of precipitated white crystals by filtration gave 3.4 of the aimed compound. mp. gradual decomp. starting at about 295° C. TLC, Rf=0.47 (n-butanol/acetic acid/water=4/1/2).

Example 19

N-(6,8-dimercaptooctanoyl)aspartylglycine disodium/ zinc chelate compound

Using 2.1 g of DL-α-lipoic acid and 2.1 g of L-aspartylglycine, 3.1 g of white crystals of the aimed compound were obtained via N-(α-lipoyl)aspartylglycine sodium salt in the same manner. mp: gradual decomp starting at about 270° C. TLC, Rf=0.54 (n-butanol/acetic acid/water=4/1/2).

Example 20

N-(6,8-dimercaptooctanoyl)threonylglycine sodium/zinc chelate compound

Using 2.1 g of DL-α-lipoic acid and 2.1 g of L-threonylglycine, 2.6 g of pale yellow crystals of the aimed compound were obtained. mp: gradual decomp. starting at about 260° C. TLC, Rf=0.60 (n-butanol/acetic acid/water=4/1/2).

Example 21

6,8-dimercaptooctanoic acid ethanolamine salt zinc chelate compound (also named as dihydrolipoic acid monoethanolamine salt zinc complex)

6.2 g of DL-α-lipoic acid was dissolved in 70 ml of methanol, and to this were added 3.5 g of zinc powder and 15 ml of 2 N hydrochloric acid and stirred for one hour at 50° C. When the solution turned colorless, unreacted zinc was removed by filtration, and the filtrate was concentrated under reduced pressure. Addition of 150 ml of water to the oily residue, collection of thus precipitated white crystals by filtration and washing with water gave the free acid form of 6,8-dimercaptooctanoic acid zinc chelate compound.

The free acid was suspended in 150 ml of water. To this was added about 2.5 g of monoethanolamine to dissolve. Concentration under reduced pressure, addition of ethanol to the oily residue thus obtained, collection of precipitated white crystals by filtration, recrystallization from water/ethanol gave 8.5 g of the aimed compound. mp. 137-139° C.

Example 22

6,8-dimercaptooctanoic acid sodium salt zinc chelate compound 6.2 g of DL-α-lipoic acid was dissolved in 70 ml of methanol, and to this were added 3.0 g of zinc powder and 40 ml of 1 N hydrochloric acid, and stirred for one hour at 50° C.

Unreacted zinc was separated out by filtration. The filtrate was concentrated under reduced pressure and water was added. Precipitated white crystals were collected by filtration. They were suspended in 150 ml of water and dissolved at a pH of about 9 by addition of 2 N sodium hydroxide. Insoluble matters were removed by filtration and the filtrate was concentrated. Addition of ethanol to this, collection of precipitated white crystals by filtration, and recrystallized from water/ethanol gave 6.0 g of the aimed compound. mp. over 300° C. TLC, Rf=0.88 (n-butanol/acetic acid/water=4/1/2).

Example 23

6,8-dimercaptooctanoic acid ethyl ester zinc chelate compound 3.5 g of DL-α-lipoic acid ethyl ester was dissolved in 60 ml of tetrahydrofuran, and to this were added 2.0 g of zinc powder and 40 ml of 70% acetic acid aqueous solution and stirred for two hours at 50° C. Unreacted zinc was separated out by filtration, the filtrate was concentrated, and water was added to this. Precipitated white crystals were collected by filtration. Recrystallized from acetic acid/water gave 3.6 g of the aimed compound. mp: gradual decomp. starting at about 290° C. TLC, Rf=0.88 (n-butanol/acetic acid/water=4/1/2).

Example 24

6,8-dimercaptooctanoic acid amide zinc chelate compound 4.2 g of DL-α-lipoic acid amide was dissolved in 70 ml of tetrahydrofuran. To this were added 2.5 g of zinc powder and 30 ml of 50% acetic acid aqueous solution and stirred for two hours at 50° C. Evaporation of the solvent, collection of precipitated crystals containing zinc, washing with water and ethanol, and recrystallization from acetic acid/water gave 4.5 g of white crystals. mp. 257-259° C. TLC, Rf=0.80 (n-butanol/acetic acid/water=4/1/2).

Preparation examples will be presented below.

| Preparation Example 1 Toilet water | |
|---|---|
| The compound of Reference Example 8 | 0.5 g |
| Glycerol | 3.5 g |
| Methyl p-hydroxybenzoate | 0.02 g |
| Propyl p-hydroxybenzoate | 0.01 g |
| Sterile purified water | to 100 ml |

| Preparation Example 2 Toilet water | |
|---|---|
| The compound of Reference Example 10 | 0.5 g |
| Propylene glycol | 3.0 g |
| Tego 51 | 0.005 g |
| Sterile purified water | to 100 ml |

| Preparation Example 3 Cream preparation | |
|---|---|
| The compound of Example 11 | 0.1 g |
| Stearic acid | 2.0 g |
| Stearyl alcohol | 7.0 g |
| Squalane | 5.0 g |
| Octyldecanol | 6.0 g |
| Polyoxyethylene cetyl ether | 3.0 g |
| Glyceryl monostearate | 2.0 g |
| Propylene glycol | 5.0 g |
| Methyl p-hydroxybenzoate | 0.05 g |
| Propyl p-hydroxybenzoate | 0.02 g |
| Sterile purified water | to 100 g |

| Preparation Example 4 Ointment | |
|---|---|
| The compound of Reference Example 7 | 1.0 g |
| Hydrophilic ointment | to 100 g |

| Preparation Example 5 | |
|---|---|
| The compound of Example 22 | 0.5 g |
| Pantothenyl alcohol | 0.5 g |
| Glycerol | 2.5 g |
| Tego-51 | 0.007 g |
| Sterile purified water | to 100 ml |

With reference to test examples below, the effect of the present invention will be demonstrated. It should be noted, however, that they are no more than illustration by examples and not intended to limit the scope of the present invention.

Test Example 1

To blotches and freckles on the face, the toilet water shown in Preparation Example 1 was applied once daily for one month. As a result, notable effect was observed in comparison with the pre-application condition, including cases of nearly disappearance and cases of fading in color to pale umber.

Test Example 2

To blotches formed on acne scars in the face, the preparation of Preparation Example 2 was applied for a month in the same manner as in Test Example 1. As a result, the blotches nearly disappeared in comparison with the pre-application condition.

Test Example 3

To deposited melanin pigment on a part of the lips, the preparation of Preparation Example 5 was applied once daily. Three months later, the black color was found eliminated.

Test Example 4

To the backs of hands which were sunburned on the seashore for two straight days, the preparation of Preparation Example 5 was applied once daily after their inflammation subsided. One month later, their color, which had been dark due to the suntan, returned to their pre-suntan tone.

Test Example 5

To a lentigo (1-mm diameter) on the arm was topically applied twice daily a preparation that was prepared according to Preparation Example 1 except that N-(6,8-dimercaptooctanoyl)histidine sodium/zinc chelate of Example 2 was used instead of N-(6,8-dimercaptooctanoyl)anthranilic acid sodium/zinc chelate of Example 2. Two months later, the black color was found eliminated leaving a subtle scar behind.

Industrial Applicability

The present compound, 6,8-dimercaptooctanoic acid zinc chelate, its derivatives and their pharmacologically acceptable salts exhibit excellent therapeutic effects in elimination of melanin pigment. Thus, they are useful in providing melanin eliminator preparations.

Some of the embodiments of the present invention were described in detail above. As it is readily possible for a person skilled in the art to make a variety of modifications and alterations to the shown embodiments without substantially departing from the novel teachings and advantages the present invention, all of such modifications and alterations are also included in the spirit and scope of the present invention that is defined by the claims below.

The present invention is based on the patent application No. 2002-307643 filed in Japan, the content of which is included in its entirety in the description of the present application.

The invention claimed is:

1. A method for elimination of melanin comprising administering to a human an effective amount of a metal chelate compound represented by the following formula (I),

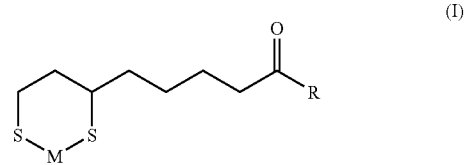

wherein M denotes a metal, and R denotes hydroxyl, O-lower alkyl, an amine selected from the group consisting of 2-aminoethanol, isopropylamine, melatonin, and 2-aminopyridine, or a peptide, wherein the amine or peptide is bonded at its nitrogen atom, or a pharmacologically acceptable salt thereof.

* * * * *